United States Patent
Kraut-Reinkober et al.

(10) Patent No.: US 12,244,433 B2
(45) Date of Patent: Mar. 4, 2025

(54) METHOD FOR FOOD MANAGEMENT, KITCHEN APPLIANCE AND FOOD PREPARATION SYSTEM

(71) Applicant: Vorwerk & Co. Interholding GmbH, Wuppertal (DE)

(72) Inventors: Stefan Kraut-Reinkober, Leverkusen (DE); Andrej Mosebach, Bochum (DE); Mirco Pieper, Wuppertal (DE); Christiane Stach, Radevormwald (DE); Wenjie Yan, Düsseldorf (DE); Sarah Werhahn, Zürich (CH)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 284 days.

(21) Appl. No.: 16/841,988

(22) Filed: Apr. 7, 2020

(65) Prior Publication Data
US 2020/0344086 A1 Oct. 29, 2020

(30) Foreign Application Priority Data
Apr. 24, 2019 (EP) .................................... 19170841

(51) Int. Cl.
*H04L 12/28* (2006.01)
*A47J 36/32* (2006.01)
(Continued)

(52) U.S. Cl.
CPC .......... *H04L 12/2829* (2013.01); *A47J 36/32* (2013.01); *A61B 5/02055* (2013.01);
(Continued)

(58) Field of Classification Search
CPC ............. H04L 12/2803; H04L 12/2823; H04L 12/2827; H04L 12/2829; H04L 2012/2847; A47J 36/00; A47J 36/32
See application file for complete search history.

(56) References Cited

U.S. PATENT DOCUMENTS

2016/0270592 A1* 9/2016 Sauerwald ............... A47J 43/04
2019/0213914 A1* 7/2019 Vallance ............. H04L 12/2827
(Continued)

FOREIGN PATENT DOCUMENTS

| CN | 103577671 A | 2/2014 |
|---|---|---|
| CN | 105652680 A | 6/2016 |

(Continued)

OTHER PUBLICATIONS

Li, Bojun, Piyanuch Hathaipontaluk, and Suhuai Luo. "Intelligent oven in smart home environment." 2009 international conference on research challenges in computer science. IEEE, 2009. (Year: 2009).*
(Continued)

*Primary Examiner* — Son T Le
*Assistant Examiner* — Matthew W. Baca
(74) *Attorney, Agent, or Firm* — Rudy J. Ng; Bret E. Field; Bozicevic, Field & Francis LLP (57) ABSTRACT

Provided is a method for food management with a kitchen appliance for at least partially automated processing of a recipe. The method includes the following steps: receiving user-specific health data that can be assigned to a user profile, and generating an evaluation of the health data for the user profile by a computing unit. The present disclosure also provides a kitchen appliance for preparing food and a system for preparing food with the kitchen appliance.

17 Claims, 4 Drawing Sheets

(51) Int. Cl.
  *A61B 5/00*  (2006.01)
  *A61B 5/0205*  (2006.01)
  *G16H 20/60*  (2018.01)

(52) U.S. Cl.
  CPC .......... *A61B 5/4872* (2013.01); *A61B 5/7475* (2013.01); *G16H 20/60* (2018.01); *H04L 2012/2847* (2013.01)

(56) References Cited

U.S. PATENT DOCUMENTS

| | | | | |
|---|---|---|---|---|
| 2019/0313844 | A1* | 10/2019 | Nadendla | A47J 36/32 |
| 2020/0065682 | A1* | 2/2020 | Paulina | G16H 20/70 |
| 2020/0280821 | A1* | 9/2020 | Chon | H04W 4/38 |
| 2022/0022778 | A1* | 1/2022 | Gauthier | G16H 50/30 |

FOREIGN PATENT DOCUMENTS

| | | |
|---|---|---|
| CN | 107633875 A | 1/2018 |
| CN | 108338679 A | 7/2018 |
| DE | 102017112855 A1 * | 12/2018 |
| EP | 3351857 A1 | 7/2018 |
| WO | WO2017055317 A1 | 4/2017 |

OTHER PUBLICATIONS

Office Action for European Application No. 19170841.1 mailed May 31, 2022, with its English summary, 6 pages.
First Office Action for Chinese Application No. 202010321493.4 mailed Jun. 2, 2022, with its English translation, 13 pages.
Second Office Action for Chinese Application No. 202010321493.4 mailed on Nov. 15, 2022, with its English Translation, 16 pages.
Office Action for European Application No. 19170841.1 mailed on Jun. 28, 2023, with its English Translation, 8 pages.
Rejection for China Application No. 202010321493.4 mailed on Apr. 4, 2023, with its English summary and translation, 18 pages.
Office Action for European Patent Application No. 19 170 841.1, mailed Jul. 1, 2024, and its English translation, 8 pages.

* cited by examiner

METHOD FOR FOOD MANAGEMENT, KITCHEN APPLIANCE AND FOOD PREPARATION SYSTEM

The invention relates to a method for food management, a kitchen appliance for preparing food and a system for preparing food with a kitchen appliance.

Kitchen appliances for preparing food are known from the state of the art. More and more functions are being integrated into kitchen appliances to enable a user to prepare food with ease. For example, some kitchen appliances can process recipes independently by automatically heating or mixing ingredients in the kitchen appliance or the like.

In addition, it is becoming increasingly common, e.g. via fitness wristbands, users' daily routines are being interfered with in order to optimize them and thereby improve the health and/or well-being of the users. This is known from the food sector, e.g. from US 2016/0048720 A1, where a user of a kitchen appliance is shown key data of utilized food, which also contains health data. This enables the user to quickly see whether the food fits into their current nutritional plan. The disadvantage is that the user is not supported in processing the displayed data. Rather, the user themself is dependent on the data being utilized for their own purposes. For example, it is desirable to automatically offer support to a user who is less creative in the selection of their food with regard to their health.

It is an object of the present invention to remedy, at least in part, any prior disadvantages known from the prior art. In particular, it is an object of the present invention to support at least one user of a kitchen appliance in the choice of their diet with regard to their health.

The preceding object is solved by a method with the characteristics of independent method claim, a kitchen appliance with the characteristics of the independent device claim and a system with the characteristics of independent system claim. Further features and details of the invention result from the dependent claims, the description and the drawings. Features and details which have been described in connection with the method according to the invention are of course also in connection with the kitchen appliance and/or the system according to the invention and vice versa, so that with regard to the disclosure of the individual aspects of the invention, reference is or can always be made to each other.

According to the invention, the method for food management with a kitchen appliance for at least partially automated processing of a recipe includes the following steps:

Receiving user-specific health data that can be assigned to a user profile,
Generation of an evaluation of the health data for the user profile by a computing unit,
Determining a recipe suggestion based on the evaluation of health data,
Output of the recipe suggestion at a user interface of the kitchen appliance.

Preferably, the method steps are performed in the order listed.

The kitchen appliance can also be described in particular as a kitchen appliance, cooker-mixer or intelligent oven. For at least partially automated processing of the recipe, it may be provided that the kitchen appliance has a mixer for mixing ingredients of the recipe and/or a heating element for heating ingredients of the recipe. Furthermore, further functional units for the automatic execution of preparation steps are conceivable. The receipt of the user-specific health data, which can be assigned to the user profile, can at least partially be done via a communication interface of the kitchen appliance. Thus, the health data can already be connected to the user profile and stored, for example, on a server or on the kitchen appliance itself. It is also conceivable that the health data will be assigned to the user profile after receipt. For example, it is possible that a user enters the health data via the kitchen appliance or a user device and thereby assigns it to the user profile. The evaluation of the health data may in particular include user classification. It is conceivable, for example, that certain classification data may be assigned to a user during the evaluation, such as "diabetics, allergy sufferers, athletes and/or the like". Furthermore, it is conceivable that certain nutritional parameters are generated during the evaluation which are considered when recommending a recipe in order to improve the user's health. If the evaluation of the health data shows, for example, that the user has an iron deficiency, this can lead to particularly iron-rich recipe suggestions. In particular, the recipe suggestion can include a concrete recipe proposal, an adaptation and/or a modification of an existing recipe and/or a proposal for a recipe classification. It is also conceivable that certain recipes with ingredients that can trigger an allergy and/or intolerance in the user are deliberately avoided or that comparison suggestions are offered for recipes without these allergenic ingredients. In particular, the recipe proposal may include a recipe that can be executed on the kitchen appliance. The recipe classification may include, for example, "low-carb" recipes, vegetarian recipes and/or the like. In particular, the generation of the evaluation and the determination of the recipe suggestion can be performed simultaneously, whereby, for example, the evaluation can be performed directly with regard to the recipe suggestion. For the output of the recipe suggestion at the user interface of the kitchen appliance it may be provided that the user interface has a display on which the recipe suggestion can be shown. In particular, it may be provided that the user can interact with the kitchen appliance via the user interface in order to react to the recipe suggestion, for example by accepting or rejecting the recipe suggestion. It may also be provided that the recipe suggestion is additionally shown on another display, e.g. via an app on a user device. A user device can include a smartphone, tablet, computer and/or similar.

Thus, the user's diet can be positively influenced in a convenient way. Because the health data is automatically evaluated and leads to a recipe suggestion, the user can also be offered recipes which were previously unknown to him or which have been forgotten. By issuing the recipe suggestion of a user interface of the kitchen appliance, the possibility is generated that the user can execute the steps directly at the kitchen appliance and thus can conveniently access the recipe or the recipe suggestion. However, this can generate a closeness to the actual cooking method, which can lower the inhibition threshold to actually consider the recipe suggestion and implement the underlying recipe. At the point of evaluating the health data and/or determining the recipe suggestion, this can preferably be done on the kitchen appliance itself, a server and/or a user device of the user. If the steps are performed on the kitchen appliance itself, it can be autonomous to an Internet connection, i.e. in particular it can be operated independently of an Internet connection. By executing the steps on a server, the advantage can be achieved that the computing capacity of the kitchen appliance can be outsourced, so that a computing unit of the kitchen appliance can be small. Furthermore, further data, especially in the context of a big-data analysis, can be included in the evaluation and/or recipe suggestion. By connecting a user device, remote access to the user profile can be enabled, so that the user can manage the user profile conveniently.

The invention may also provide that the health data include vital data of a user. The vital data may in particular includes values concerning blood sugar, weight, blood pressure, intolerances, allergies of substances and/or the like. Furthermore, it is conceivable that the vital data may include further characteristics of the user, such as an age and/or the like. Furthermore, the vital data may include activity data, whereby the activity data may be received, for example, from a fitness wristband, from calendar data of the user and/or other data sources. In particular, the vital data can thus be static or dynamically changing health values of the user, which can provide information about the current state of health of the user. Thus, the recipe suggestion can be individually adapted to the user's needs in order to enhance a positive influence on the user's diet.

A method according to the invention may further provide that the generation of the evaluation includes a comparison of the health data with reference data and/or that the generation of the evaluation considers a user response and/or a change in vitality to a previous recipe suggestion and/or to a previous activity suggestion. In this way, boundary conditions can be set for the evaluation in the form of the reference data, the user response and/or the vital sign change. It is also conceivable that the vital sign change and/or the user response can be considered when determining the recipe suggestion. The reference data can, for example, be ideal parameters that correspond to the health data. For example, the evaluation may include comparing a user's blood glucose value with a blood glucose value that is ideal for a user in their age category and/or weight category. The user response can include, for example, whether the user accepts the recipe suggestion and actually executes the underlying recipe. The change in vital signs can, for example, include a change in the health data after the recipe suggestion has been executed. Furthermore, the vital sign reaction to an earlier activity suggestion can be determined and considered. If, for example, it is determined that the user gains weight although this was not desired, conclusions can be drawn for future recipe suggestions. This can result in a learning effect when the method is performed, so that the recipe suggestion, especially after a learning phase, provides the user with a high degree of accuracy in the selection of recipes for the recipe suggestion. Furthermore, the user response can also be utilized to consider a user's preferences. If the user rejects, for example, recipe suggestions with a certain ingredient several times, it can be concluded that this does not correspond to the user's preferences and therefore recipes with such ingredients will be given lower priority or avoided in the future. In particular, the user response and/or the vital change can be added to the reference data to be available for further evaluations.

Furthermore, in the case of a method according to the invention, it may be provided that the method includes the following step:

Evaluation of historical data of previously performed cooking methods and/or previously utilized food, whereby the history data is considered when creating the recipe suggestion. The history data can be determined, for example, by recording or saving previously executed recipes. Previously utilized foods can be detected, for example, by a camera, a barcode scanner, an ultrasonic sensor, a radar sensor, in particular a short-range radar sensor, a scale, preferably with at least three load cells, and/or other sensors. It is also conceivable that the cooking methods previously performed and/or the food previously utilized could be evaluated on the basis of data from delivery services. Thus, history data provided by third parties can also be utilized to improve the evaluation of health data and/or recipe suggestion.

Within the scope of the invention, it is also conceivable that the method includes the following step:

Determination of position information of the kitchen appliance and/or a user, whereby the position information is considered when creating the recipe suggestion. The position information can be determined in particular by a GPS sensor in the kitchen appliance and/or in a user device. Furthermore, it is conceivable that the position information can be determined by a network location of the kitchen appliance and/or user device, in particular by means of an IP address and/or mobile radio data. The position information may in particular include the location of the kitchen appliance and/or activity data of the user. For example, the position information can be utilized to determine whether the user has been active in sports or has visited certain restaurants. This can be processed accordingly with the health data and lead to improved recipe suggestions. For example, the location of the kitchen appliance can be utilized to determine in which region the kitchen appliance is located, so that conclusions can be drawn about the general sensitivities of the population in this region in order to improve recipe suggestion.

Preferably, in the case of a method according to the invention, the method may include the following step:

At least partially automated processing of the recipe suggestion by the kitchen appliance.

Thus, the user's inhibition threshold to follow the recipe suggestion can be lowered if the kitchen appliance starts the recipe suggestion automatically and/or can execute it at least partially automatically. This can motivate the user, for example, to try out new recipes in the context of recipe suggestion if the preparation method itself is simplified. Furthermore, the recipe suggestion can be integrated more easily into the user's everyday life.

Furthermore, a method according to the invention may provide that the determination of the recipe suggestion includes at least one of the following steps:

Selection of a recipe from a recipe database based on the evaluation of health data, a user goal and/or a vital change, Generation of a recipe based on the evaluation of health data, a user goal and/or a change in vital signs, in particular whereby the history data is considered when generating the recipe.

In particular, the change in vital signs may be a change in the user's vital signs to a previous recipe suggestion. The user goal can preferably be specified manually. The generation of the recipe can, in particular, involve a modification of an existing recipe. Preferably, an individual menu composition based on the user's requirements can be generated during generation. The history data can be utilized in particular to determine the preferences. When generating the recipe, a behavior pattern of the user is preferably analyzed using the history data in order to identify their preferences. If the recipe is selected from the recipe database on the basis of the evaluation of health data, the user's goal and/or the change in vitality, it is also possible to fall back on existing recipes that have already proven to be advantageous for other users, for example. For this purpose, it can be provided that the recipes in the recipe database are selected on the basis of keywords.

Within the scope of the invention, it may also be provided that an external receiving of the health data by the device interface is possible and an external transmission of the health data is at least partially prevented, in particular wherein the external transmission of the health data can be enabled or selectively enabled by the user. The external transmission of the health data can be understood to mean that the health data are sent from the kitchen appliance and/or from a server and are received by entities, in particular external service providers, which are not directly assigned to the user profile. These may be, for example, doctors, a fitness studio, delivery services, an insurance company and/or other external service providers. If only receiving but not sending is possible, data can be received from the external service providers that can improve the recipe suggestion and provide further information about the user's state of health. At the same time, data security can be ensured if this data cannot be read by the external entities. In particular, activation by the user may enable the user to manage their data independently and, for example, to allow only those services to access the data that they trust. Selective activation can be understood to mean that only certain data can be shared with external services and/or data can only be sent to certain services. Since health data are particularly sensitive data, increased data security can also lead to an improved acceptance of the entire method involving the processing of health data.

Preferably, in a method according to the invention, it may be provided that the health data includes activity data of a user and the receiving of the health data includes the following step:

Recording of activity data.

Activity data may include, in particular, the user's activities away from home, such as restaurant visits, meals at friends and relatives and/or similar. This can be utilized to receive further data and thus improve the recipe suggestion in relation to the user. Furthermore, the activity data can also include the user's sporting activities, so that, for example, to support the user's muscle development depending on the sporting activity, the recipe suggestion prefers protein-rich food. In particular, the activity data can be utilized to consider further health data.

Furthermore, in a method according to the invention, it is conceivable that the receipt of health data is effected via a sensor unit, in particular wherein the sensor unit includes a user device and/or one of the following sensors:

Camera,
GPS sensor,
Scales,
Temperature sensor (especially contactless, e.g. infrared measurement)
Heart rate monitor,
Blood glucose sensor,
Blood pressure sensor,
Pulse sensor,
Body fat sensor.

The sensor unit can be provided for this purpose on a fitness wristband, a Smartwatch, a Smartphone and/or similar. In particular, actual measured values, in particular related to the current state of health of the user, can thus be considered for the generation of the recipe suggestion. For example, it is not necessary for the user to enter the health data manually, but these data can be received in real time. Thus, for example, the frequency of health data recording can be increased, thus improving the accuracy of the evaluation. Furthermore, the user comfort can be improved by a sensor close to the user. In particular, further data, such as position information, can also be recorded by the sensor unit.

Furthermore, in the case of a method according to the invention, it is conceivable that the method includes the following step:

Receive a user's goal that can be assigned to the user profile, whereby the user's goal is considered when determining the recipe suggestion. For example, the user goal may include losing weight up to a target weight, participating in a sports event and/or a certain fitness level. This can improve the user's motivation to follow the recipe suggestion if the user's ambition is stimulated. Furthermore, the recipe suggestion can be improved by tailoring it to an individual, subjective need of the user and thus improving the user's health in a certain aspect. In particular, the user goal and/or progress can be provided, in particular displayed, at the user interface.

Furthermore, a method according to the invention may provide that a recipe sequence is determined depending on the health data, the position information and/or the user's goal. Preferably the recipe sequence includes several recipe suggestions. The recipe sequence may in particular includes a type of recipe playlist in which the user may be surprised by possibly unknown recipes. The sequence of the recipe sequence can be variable or predefined. In particular, the recipe sequence can be made available to the user at the user interface and/or a user device of the user. Thus, several recipe suggestions can be given for future meals of the user. Thus, the nutritional behavior of the user can be improved in the long run and at the same time the user can be provided with the comfort of knowing the recipe suggestions for several days in advance and thus be able to adjust their shopping accordingly.

Furthermore, in methods according to the invention it can be provided that the recipe sequence is modified depending on a user response and/or a change in vitality to a recipe suggestion, in particular the specific and/or an earlier recipe suggestion of the recipe sequence. If, for example, it is determined that the user rejects a recipe suggestion of the recipe sequence or their health data do not improve or even worsen, the recipe sequence can be modified accordingly. Furthermore, recipe suggestions can be replaced and/or modified within the recipe sequence. In particular, an adaptation can thus be achieved in order to achieve the user goal as efficiently as possible.

Furthermore, in the case of a method according to the invention, it is conceivable that a user group, in particular a household, is assigned to the user profile. In this way, it is not necessary for each user to generate a separate user profile. Instead, a household can be grouped together in a user group. In this way, you can manage the individual users within the user profile, and coordinate their habits and/or user goals. For example, if the user group is a family, the health of all or as many members of the user group as possible can be improved.

Within the scope of the invention, it is also conceivable that the method includes the following steps:

Determination of an activity suggestion based on the evaluation of the health data,
Output of the activity suggestion, especially at the user interface of the kitchen appliance.

Activity suggestion can improve the user's health by optimizing the user's behavior, especially in addition to the recipe suggestion. The output of the activity suggestion can take place at the user interface of the kitchen appliance and/or at a user device of the user. If, for example, the user's goal is to participate in a marathon, the activity suggestion can, for example, specify a training plan and the recipe suggestion can at the same time improve the user's nutritional behavior in accordance with this training plan. In this way, the user's overall health can be improved.

According to another aspect of the invention, a kitchen appliance is required for the at least partially automated processing of a recipe. According to the invention, the kitchen appliance has a functional unit for processing ingredients and a user interface for interaction with a user. Furthermore, the user interface is connected to an integrated control unit by means of which a method according to the invention can be initiated, in particular performed.

Initiation of the method can preferably be understood to mean that the method can be triggered or set in motion by the integrated control unit of the kitchen appliance. It is thus conceivable that the integrated control device is configured to communicate with a server and to control the server in such a way that the method is at least partially or completely performed on the server. Finally, the recipe suggestions or the recipe suggestion can be provided via the user interface. The user interface can preferably have a display and/or a control element, whereby the display can preferably be a touch display. This allows a user to interact with the kitchen appliance in a convenient way and to transmit control commands to the integrated control unit of the kitchen appliance. The integrated control device can preferably be understood as an internal control device of the kitchen appliance, which is permanently installed with the kitchen appliance. The functional unit for processing ingredients can be configured to enable at least partially automated processing of a recipe by performing certain recipe steps such as, for example, heating of ingredients, mixing of ingredients and/or the like in dependence on an activation by the integrated control device. For this purpose, the functional unit may have, for example, a mixer and/or a heating element. Preferably, the integrated control unit can be utilized to perform the method, in particular completely on the kitchen appliance. This means that it is not necessary, for example, to connect the kitchen appliance to the Internet in order to access a server and use its computing power. Furthermore, it can also enable a user to operate the kitchen appliance independently of the Internet connection, e.g. directly after purchase. Thus, a kitchen appliance according to the invention brings the same advantages as those already described in detail with respect to a method according to the invention.

According to another aspect of the invention, a system for preparing food is required. The system includes a kitchen appliance, in particular a kitchen appliance according to the invention, for at least partially automated processing of a recipe. The kitchen appliance includes a functional unit for processing ingredients and a user interface for interaction with a user. Furthermore, the system has a storage unit in which a user profile and user-specific health data can be stored. Furthermore, the system includes a computing unit which is configured to generate an evaluation of the health data and to determine and output, in particular display, at the user interface depending on the evaluation of a recipe suggestion.

Preferably, it may also be provided that the processing unit is configured to provide a user device with the recipe suggestion via a communication. This can enable the user to access the recipe suggestion remotely. In particular, the recipe suggestion can be available on an external display of the user device and/or by accessing an app on the user device. In particular, it may be possible for a method according to the invention to be executed by the computing unit. Thus, a system according to the invention brings the same advantages as those already described in detail with regard to a kitchen appliance according to the invention and/or a method according to the invention.

Preferably, a system according to the invention may provide that the computing unit and/or the storage unit can be in communication with another kitchen appliance and/or a user device for the recording of user-specific health data. In particular, it is conceivable that the storage unit is a storage chip that can be connected to the kitchen appliance, in particular via the appliance interface. The user device may preferably include a fitness wristband, a smartphone, a tablet and/or the like. In particular, the communication may also enable the user to have remote access to the computing unit and/or remote display of the computing unit via a display and/or an app of the user device. For the communication connection, the system, in particular the kitchen appliance, can have an appliance interface through which the kitchen appliance can be in communication with the other kitchen appliance and/or the user device. By recording user-specific health data on a further kitchen appliance and/or a user device, it is also possible for a user to transmit the health data for processing in accordance with a method according to the invention if, for example, they cook while traveling or on a further kitchen appliance. It is conceivable, for example, that the additional kitchen appliance is set up at the user's place of work, so that the user-specific health data can be recorded both from home and at work. In this way, the user's diet can be shown in a great deal of detail. Furthermore, the user device can also enable control of the nutritional data or health data while traveling.

Preferably, a server is provided for in a system according to the invention, which includes the computing unit and/or the storage unit. Alternatively, the computing unit and/or the storage unit can be part of the integrated control unit of the kitchen appliance. If the computing unit and/or the control unit is at least partially outsourced to the server, a central computing capacity of the server can be utilized and the kitchen appliance can be smaller in computing power. This can result in cost advantages of the kitchen appliance and access to further data, especially to further databases, can be facilitated by the server.

Furthermore, in a system according to the invention, it may be provided that the kitchen appliance has an appliance interface by means of which the kitchen appliance can be in communication with the computing unit and/or the storage unit, in particular for accessing a recipe database. In particular, the server may also have a corresponding interface for this purpose. The appliance interface can be a wired or a wireless appliance interface, in particular it is conceivable that the kitchen appliance can be in communication with the computing unit and/or the storage unit via a network, in particular an Ethernet connection, a WLAN connection, a mobile radio connection and/or the like. Furthermore, it is conceivable that the computing unit and/or the storage unit can be in communication with the kitchen appliance via a local connection. Thus, the appliance interface can be, for example, a USB interface, a Bluetooth interface and/or the like. This can easily enable a corresponding communication.

Further measures to improve the invention are described in the following description of some embodiments, which are shown schematically in the figures. All features and/or advantages arising from the claims, the description or the drawings, including constructional details, spatial arrangements and method steps, may be essential to the invention, both individually and in various combinations. It should be noted that the figures are descriptive only and are not intended to limit the invention in any way. It shows schematically:

In the following figures, for the same technical characteristics, also of different embodiments, the identical reference characters are utilized.

Figure 1:
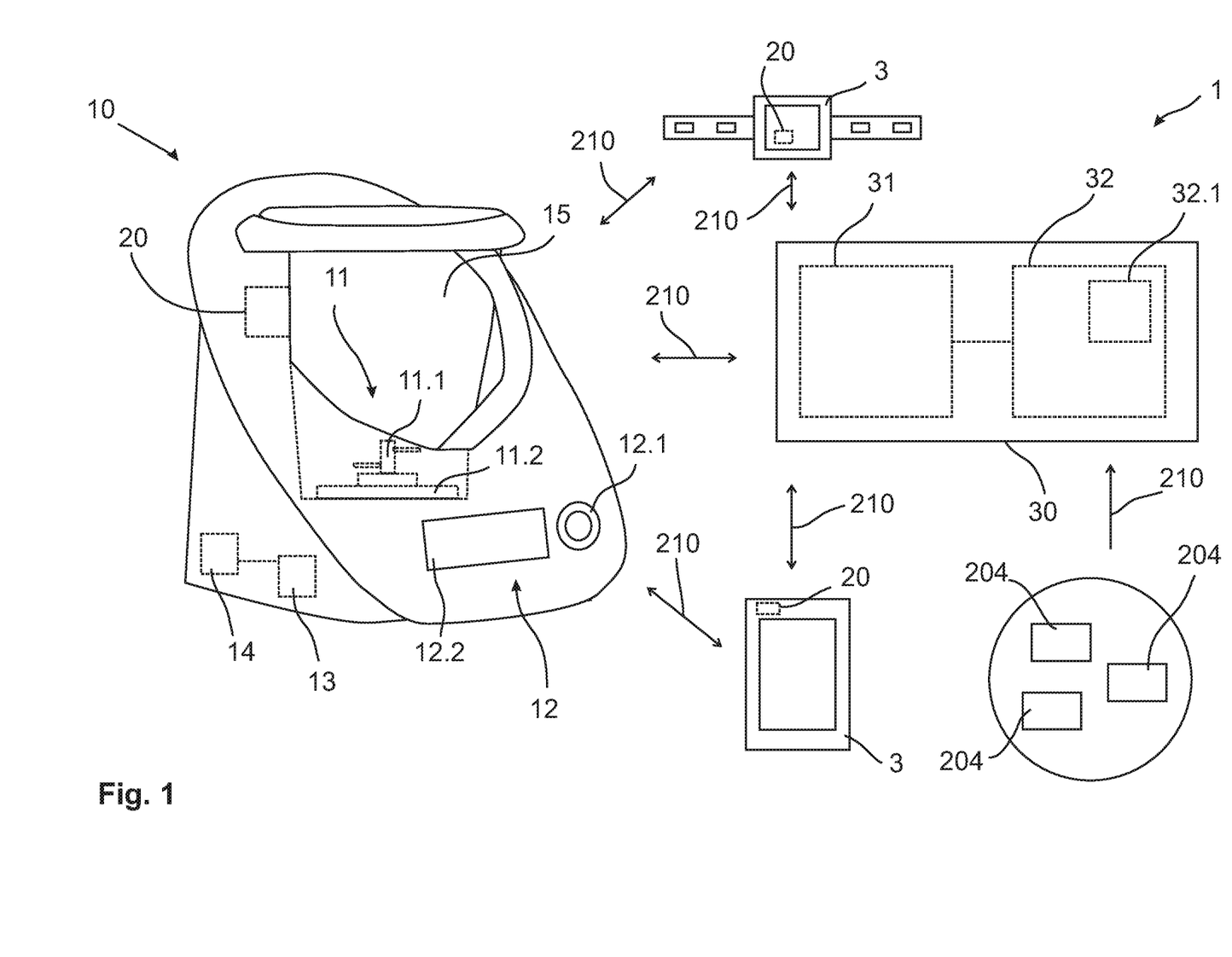
FIG. 1 an inventive system comprising an inventive kitchen appliance for performing an inventive method in a first embodiment, FIG. 2 the method of the first embodiment in schematic representation of the method steps, FIG. 3 an evaluation of health data in the method of the first embodiment, FIG. 4 a user profile in the inventive step of the first embodiment, FIG. 5 an interaction with an external service provider in the method of the first embodiment, FIG. 6 a system according to the invention with a kitchen appliance according to the invention in a further embodiment.

FIG. 1 shows a system 1 for preparing food according to the invention in a first embodiment. The system 1 includes a kitchen appliance 10 according to the invention for at least partial automating and processing of a recipe. For this purpose, the kitchen appliance 10 also has a functional unit 11, which includes a mixer 11.1 and a heating element 11.2. Preferably, the functional unit 11 is arranged in a cooking vessel 15 of the kitchen appliance 10 so that a user can load ingredients into the cooking vessel 15 and then control the functional unit 11 via a user interface 12 of the kitchen appliance 10. For this purpose, for example, a recipe can be selected and started on a display 12.2 of the user interface 12 using a control element 12.1. The ingredients in a cooking vessel 15 can then be mixed by the mixer 11.1 and heated by the heating element 11.2. Furthermore, the kitchen appliance 10 has an appliance interface 14, through which the kitchen appliance 10 can be in communication with a server 30 and/or a user device 3. For this purpose, the kitchen appliance 10 can be connected to the Internet via the appliance interface 14, for example. Furthermore, the kitchen appliance 10 has an integrated control unit 13 by means of which a method 100 according to the invention can at least be initiated. A computing unit 31 of the server 30 can be controlled by the control unit 13 in order to execute the method 100.

Figure 2:
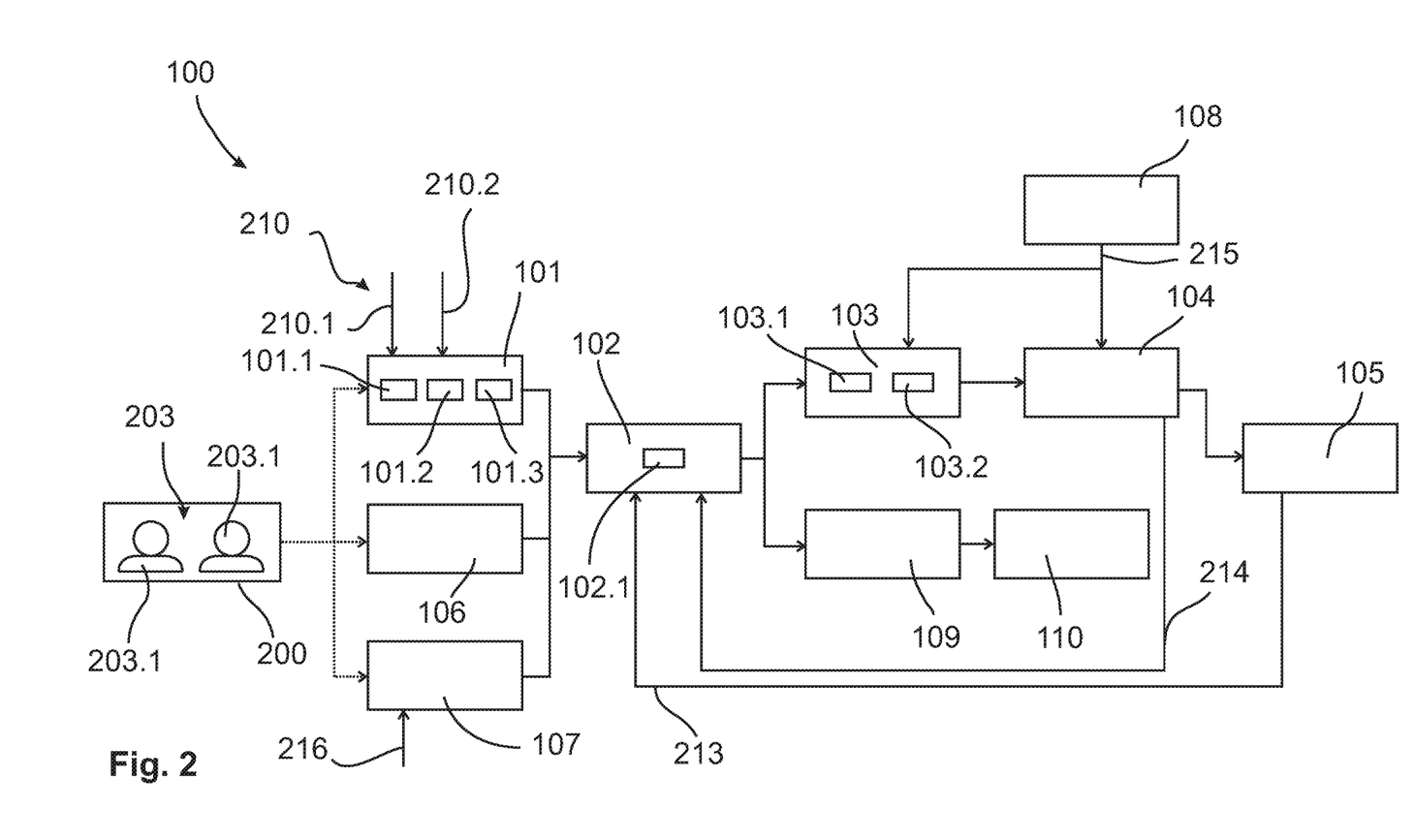

The method 100 is shown in FIG. 2. The method involves receiving 101 user-specific health data 210, which can be assigned to a user profile 200. In particular, the health data 210 can be assigned to user profile 200 when this is retrieved. For example, retrieving user profile 200 may require the user to enter login data, especially on a kitchen appliance 10. This can ensure that only the user can access their own data. It is also conceivable that user profile 200 could include a user group 203 with several individual users 203.1. This means that a household can be represented by user profile 200, for example. Health data 210 can preferably include vital signs 210.1 and activity data 210.2. The user's vital sign data 210.1 can, for example, include medical values such as a blood sugar level, an average pulse rate and/or the like. For this purpose, a recording 101.3 of the activity data 210.2, e.g. in the form of a frequency of sports activities, stress and/or sleeping times, may be provided. In particular, the health data 210, as shown in FIG. 1, may be recorded and/or made available by a user device 3, preferably in the form of a fitness wristband, a smartphone or tablet. Health data 210 can be received via a sensor unit 20, which is part of the user device 3 and/or the kitchen appliance 10. The sensor unit 20 may include, for the purpose of receiving the health data 210, e.g. a camera, a GPS sensor, a scale, a heart rate sensor, a blood sugar sensor, a pulse sensor and/or a body fat sensor. In particular, the user device 3 itself may form the sensor device 20. It is also conceivable that user device 3 communicates with server 30 and the health data 210 is made available to a kitchen appliance 10 via server 30 or remains on a kitchen appliance 10 to continue the method 100. Furthermore, it is possible that an evaluation 106 of history data 220 is performed, whereby the history data 220 may include e.g. cooking methods performed and/or food previously utilized. In this way, in addition to the current health data 210, it may be possible to draw conclusions about the user's diet, whereby the history data 220 can be correlated with the user-specific health data 210 when generating 102 an evaluation 211 at least the health data 210 for the user profile 200. Furthermore, evaluation 211 is shown again in FIG. 3, where health data 210 in the form of vital data 210.1 and/or activity data 210.2 are utilized in evaluation 211. Furthermore, e.g. vital change 213 and reference data 212 can be considered in evaluation 211. In addition, a determination 107 of position information 216 can be provided, which can also be included in evaluation 211. The position information 216 can show a location of the user in a certain region, so that regional influences on health can be considered. Furthermore, the position information 216 can be part of the activity data 210.2. Preferably, a comparison 102.1 of health data 210 with reference data 212 is performed within the scope of evaluation 211. The reference data 212 may, for example, include ideal data which should be available from a user of the same age, profession and/or similar. As a result, there may be a difference between the available health data 210 and reference data 212, which represents a state of health to be optimized.

Figure 3:
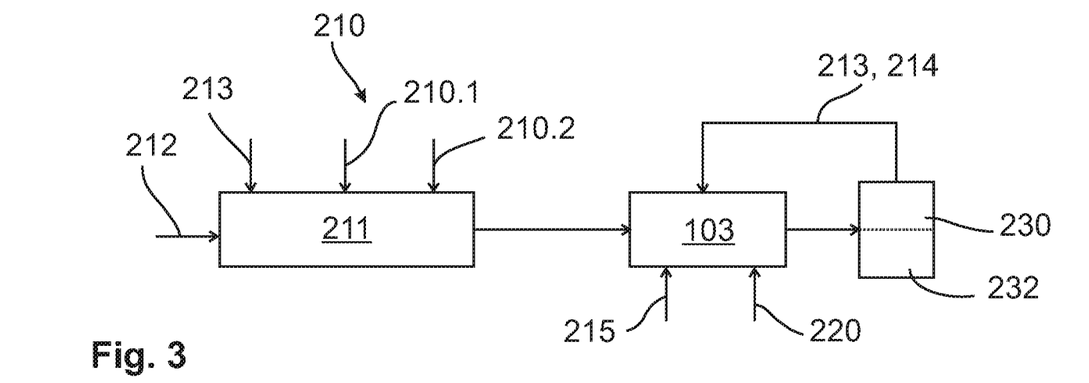

Based on evaluation 211, a recipe suggestion 230 is determined 103, whereby preferably a selection 103.1 of a recipe from a recipe database 32.1 and/or a generation 103.2 of a recipe using evaluation 211 is performed. Preferably, history data 220 can be considered when generating 103.2 the recipe. The recipe database 32.1 can preferably be part of a storage unit 32 of server 30. Afterwards, an output 104 of the recipe suggestion 230 is issued at the user interface 12 of the kitchen appliance 10, so that the user can use the recipe suggestion 230 directly at the kitchen appliance 10 if he wants to follow the recipe suggestion 230 and prepare the corresponding meal at the kitchen appliance 10. Consequently, in particular depending on a user response 214, an at least partially automated processing 105 of recipe suggestion 230 can be performed by kitchen appliance 10. User response 214 can, for example, confirm or reject recipe suggestion 230. The positive or negative user response 214 can be utilized for the next evaluation 211 within reference data 212 and/or history data 220 to consider the user preferences. If a processing 105 of the recipe suggestion 230 is performed, it may also be provided that a vital reaction 213 of the user is measured and is also considered in the next evaluation 211. Thus, for example, it is conceivable that the user's blood sugar level increases to a certain extent on the basis of recipe suggestion 230 and thus it is known at the next evaluation 211 to what extent the health data 210 have an individual effect on the user depending on certain foods. In order to further improve recipe suggestion 230, it may be necessary to receive 108 a user goal 15 that is assigned or can be assigned to user profile 200. In particular, the user can add user goal 215 to user profile 200, e.g. via user device 3 or user interface 12, so that user goal 215 is considered when determining 103 of recipe suggestion 230. User goal 215 may include, for example, a certain fitness level and/or the like. Based on the evaluation 211, an activity suggestion 232 can also be determined according to step 109 and an output 110 of the activity suggestion 232 can be made on user device 3 and/or user interface 12 of kitchen appliance 10. A user response 214 and/or a change in vitality 213 can also be made to the activity suggestion 232 and considered in the next evaluation 211.

Figure 4:
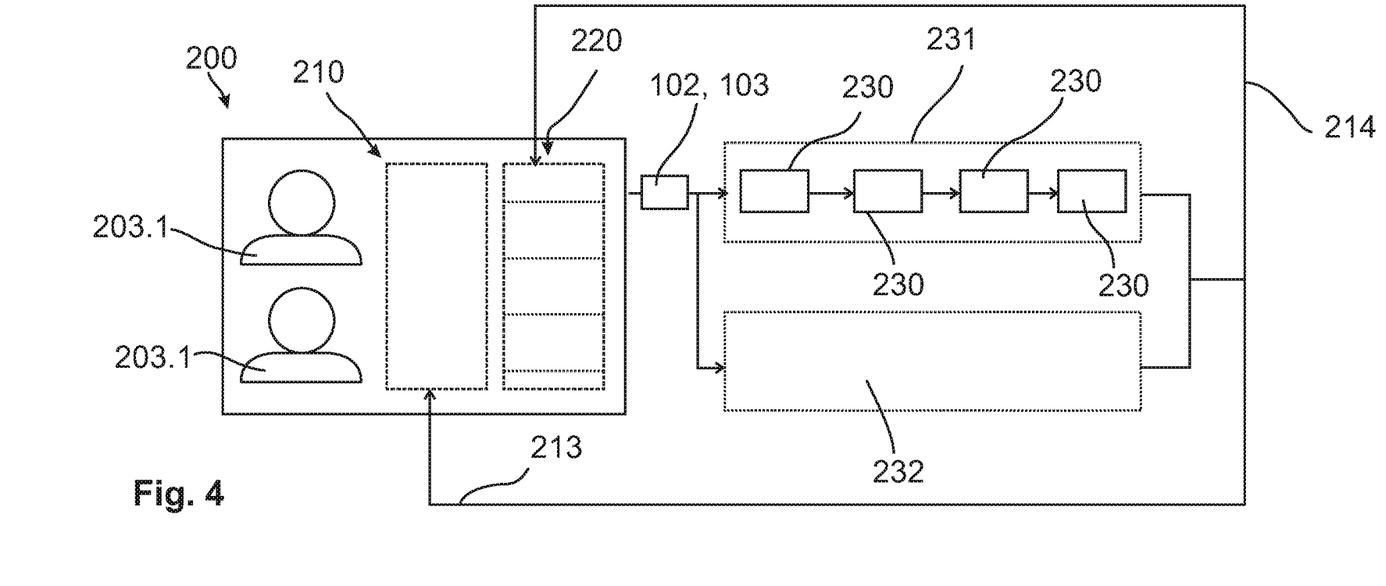

FIG. 4 shows a detailed representation of the user profile 200, to which the user-specific health data 210 and the historical data 220 are assigned. These can be processed using method 100 to generate at least a recipe suggestion 230 and preferably an activity suggestion 232, as described above. In particular, it can be provided that several recipe suggestions 230 are determined and a recipe sequence 231 is generated on the basis of the recipe suggestions 230. Recipe sequence 231 can be assigned to user profile 200, in particular depending on user response 214 and/or vital change 213. This enables the user to process several recipe suggestions 230 one after the other, for example, and the long-term influence of the food management is included in evaluation 211.

Figure 5:
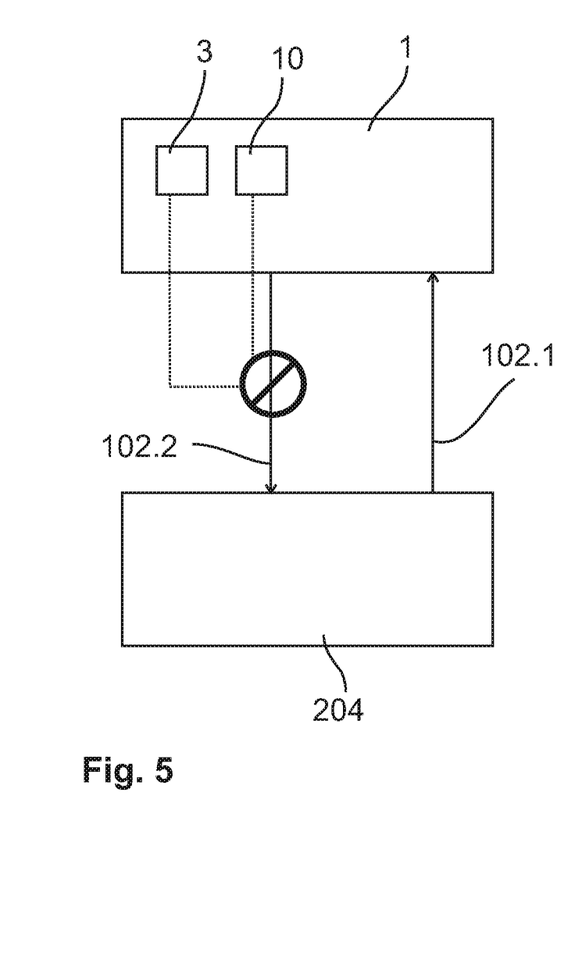

FIG. 5 also shows an interaction of system 1 with an external service provider 204, whereby external reception 101.1 of health data 210 is possible through the device interface 14 of the kitchen appliance 10 and external transmission 101.2 of health data 210 is at least partially prevented. For this purpose, the user can enable or selectively enable the external transmission 101.2 of the health data 210 to the external service provider 204 via the user interface 12 and/or the user device 3. This enables the external service provider 204, i.e. a fitness studio or a physician, for example, to provide health data 210 in order to improve nutritional control with the kitchen appliance 10. At the same time, this ensures data protection, in particular to protect health data 210 as particularly sensitive personal data.

Figure 6:
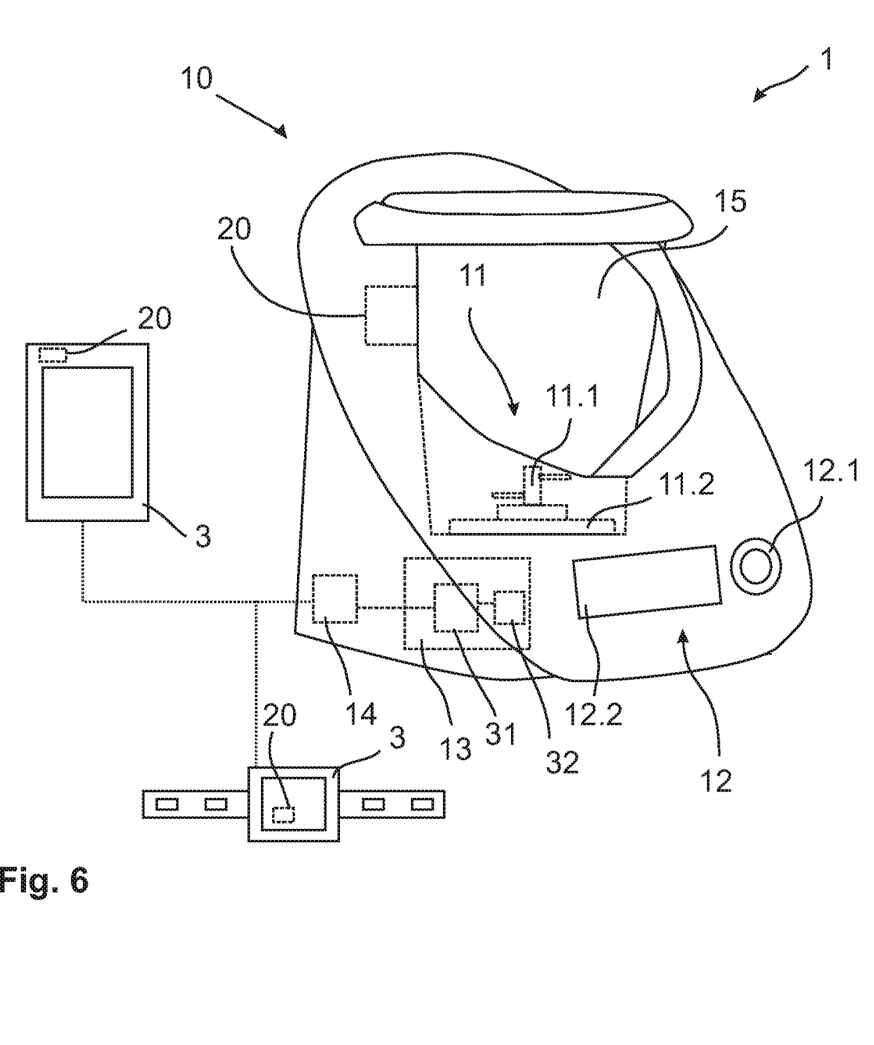

FIG. 6 also shows a system 1 according to the invention with a kitchen appliance 10 according to the invention in a further embodiment. In this case, system 1 essentially corresponds to system 1 of the first embodiment, whereby an integrated control unit 13 of kitchen appliance 10 has a computing unit 31 and a storage unit 32. In particular, the method 100 according to the invention can be completely executed on the kitchen appliance 10. User devices 3 in the form of a fitness wristband and/or a smartphone or tablet or the like can also be connected to the kitchen appliance 10 via a device interface 14 in order to exchange health data 210 with the kitchen appliance 10.

The above explanation of the embodiment describes the present invention exclusively by way of examples. Of course, individual features of the embodiments can be freely combined with each other, if technically reasonable, without leaving the scope of the present invention.

LIST OF REFERENCE SIGNS

1 System
3 User device
10 Kitchen appliance
11 Functional unit
11.1 Mixer
11.2 Heating element
12 User interface
12.1 Control element
12.2 Display
13 Control unit
14 Device interface
15 Cooking vessel
20 Sensor unit
30 Server
31 Computing unit
32 Storage unit
32.1 Recipe database
100 Methods
101 Received from 210
101.1 External receiving
101.2 External transmission
101.3 Recording of 210.2
102 Generating of 211
102.1 Compare of 210 and 212
103 Determination from 230
103.1 Selecting a recipe
103.2 Generating a recipe
104 Output of 230
105 Processing of 230
106 Evaluation of 220
107 Determining position information
108 Received from 215
109 Determine from 232
110 Output of 232
200 User profile
203 User group
203.1 Single user of 203
204 External service provider
210 Health data
210.1 Vital data
210.2 Activity data
211 Evaluation
212 Reference data
213 Vital change
214 User response
215 User goal
216 Position information
220 Historical data
230 Recipe suggestion
231 Recipe sequence
232 Activity suggestion

The invention claimed is:

1. A method for food management with a kitchen appliance for at least partially automated processing of a recipe, wherein the kitchen appliance comprises a component for executing the recipe at least partially automatically, and wherein the method comprises:

Determining position information of a user device, the position information comprising activity data of the user, the determining of the position information being performed by at least one of the following:
 a sensor of the user device determining the position information of the user device, or
 the user device analyzing network data and thereby determining the position information of the user device from a network location of the user device, wherein a computing unit of at least the kitchen appliance or a server communicating with the kitchen appliance performs:

Receiving user-specific health data that can be assigned to a user profile,

Generating an evaluation of the health data for the user profile by the computing unit, wherein the evaluation of the health data includes comparing a determined at least one user health parameter with at least one reference health parameter that corresponds to:
the at least one user health parameter; and
at least one health related category of the user,
Determining a recipe sequence comprising several recipe suggestions configured for an at least partially automatic execution by the kitchen appliance, the recipe suggestions being determined at least based on a vital change of the user to a previous recipe suggestion, the position information and the evaluation of the health data by the computing unit, wherein at least one recipe suggestion of the recipe suggestions is an existing recipe in a recipe database being assigned to be beneficial for other users and is selected from the recipe database based on the vital change of the user, and
Sending at least one of the recipe suggestions to a user interface of the kitchen appliance by the computing unit for outputting the sent at least one of the recipe suggestions at the user interface.

2. The method according to claim 1,
wherein,
at least the health data includes vitality data of a user,
or in that the generation of the evaluation includes a comparison of the health data with reference data or in that when generating the evaluation, a user response or a change in vitality of a user to a previous recipe suggestion is considered.

3. The method according to claim 1,
wherein,
the method includes the following step:
Evaluating historical data of previously performed cooking processes and previously utilized foods,
whereby at least the historical data are considered when determining the recipe suggestion, wherein the evaluation of the health data is performed depending on the previously performed cooking processes and the previously utilized foods using data from delivery services, or that the method includes the following step:
Determining position information of at least the kitchen appliance or a user, whereby at least the position information is considered when determining the recipe suggestion, or that the method includes the following step:
At least partially automated processing of the recipe suggestion by the kitchen appliance.

4. The method according to claim 1,
wherein,
determining the recipe sequence includes at least one of the following steps:
Selecting a recipe from a recipe database on the basis of at least the evaluation of the health data, a user goal or a change in vitality of a user, and
Generating a recipe using the evaluation of at least the health data of a user goal or the change in vitality.

5. The method according to claim 1,
wherein,
external reception of the health data by a device interface is possible and external transmission of the health data is at least partially prevented.

6. The method according to claim 1,
wherein,
the health data includes activity data of a user and the receiving of the health data comprises the following step:
Recording activity data.

7. The method according to claim 1,
wherein,
the receiving of the health data occurs via a sensor unit.

8. The method according to claim 7,
wherein,
the sensor unit at least comprises a user device or comprises one of the following sensors:
Camera,
GPS sensor,
Scales,
Temperature sensor
Heart rate monitor,
Blood glucose sensor,
Blood pressure sensor,
Pulse sensor, or
Body fat sensor.

9. The method according to claim 1,
wherein,
the method comprises the following step:
Receiving of a user goal which is assignable to the user profile,
whereby the user goal is considered when determining the recipe suggestion.

10. The method according to claim 9,
wherein,
a recipe sequence is determined at least as a function of the health data, the position information or the user goal,
or in that the recipe sequence is modified as a function of a user response or a change in vitality of a user to a recipe suggestion of the recipe sequence.

11. The method according to claim 1,
wherein,
a user group is assigned to the user profile.

12. The method according to claim 1,
wherein,
the method comprises the following steps:
Determining an activity suggestion based on the evaluation of the health data, and
Outputting the activity suggestion.

13. The method according to claim 1,
wherein, by the position information, it is determined whether the user visited certain restaurants, the determination, whether the user visited said restaurants, being processed with the health data to determine the recipe suggestions.

14. A kitchen appliance for at least partially automated processing of a recipe, comprising:
a component for executing the recipe at least partially automatically, and
a user interface for interaction with a user,
wherein,
the user interface is connected to an integrated control unit by means of which a method is initiated for food management with a kitchen appliance for at least partially automated processing of a recipe, comprising:
Determining position information of a user device, the position information comprising activity data of the user, the determining of the position information being performed by at least one of the following:
a sensor of the user device determining the position information of the user device, or
the user device analyzing network data and thereby determining the position information of the user device from a network location of the user device, wherein a computing unit of at least the kitchen appliance or a server communicating with the kitchen appliance performs:

Receiving user-specific health data that can be assigned to a user profile,

Generating an evaluation of health data for the user profile by the computing unit, wherein the evaluation of the health data includes comparing a determined at least one user health parameter with at least one reference health parameter that corresponds to:
the at least one user health parameter; and
at least one health related category of the user, Determining a recipe sequence comprising several recipe suggestions configured for an at least partially automatic execution by the kitchen appliance, the recipe suggestions being determined at least based on a vital change of the user to a previous recipe suggestion, the position information and the evaluation of the health data by the computing unit, wherein at least one recipe suggestion of the recipe suggestions is an existing recipe in a recipe database being assigned to be beneficial for other users and is selected from the recipe database based on the vital change of the user, and Sending at least one of the recipe suggestions to the user interface of the kitchen appliance by the computing unit for outputting the sent at least one of the recipe suggestions at the user interface.

15. A system for preparing food comprising:
a kitchen appliance, for at least partially automated processing of a recipe, comprising:
   a component for executing the recipe at least partially automatically, and
   a user interface for interaction with a user,
wherein the kitchen appliance is configured to determine position information of a user device, the position information comprising activity data of the user, the determining of the position information being performed by at least one of the following:
   a sensor of the user device determining the position information of the user device, or
   the user device analyzing network data and thereby determining the position information of the user device from a network location of the user device, wherein a computing unit of at least the kitchen appliance or a server communicating with the kitchen appliance comprises:
a storage unit in which a user profile and user-specific health data can be stored, and wherein the computing unit is configured to:
produce an evaluation of the health data for the user profile, wherein the evaluation of the health data includes comparing a determined at least one user health parameter with at least one reference health parameter that corresponds to:
   the at least one user health parameter; and
   at least one health related category of the user,
determine a recipe sequence comprising several recipe suggestions configured for an at least partially automatic execution by the kitchen appliance, the recipe suggestions being determined at least based on a vital change of the user to a previous recipe suggestion, the position information and the evaluation of the health data, wherein at least one recipe suggestion of the recipe suggestions is an existing recipe in a recipe database being assigned to be beneficial for other users and is selected from the recipe database based on the vital change of the user, and
send at least one of the recipe suggestions to the user interface of the kitchen appliance for outputting the sent at least one of the recipe suggestions at the user interface.

16. The system according to claim 15,
wherein,
at least the computing unit or the storage unit can be in communication with at least a further kitchen appliance or the user device in order to record user-specific health data,
or that the server comprises at least the computing unit or the storage unit.

17. The system according to claim 15,
wherein,
the kitchen appliance has an appliance interface by means of which the kitchen appliance can be in communication with at least the computing unit or the storage unit.

* * * * *